US00PP09675P

United States Patent [19]

Drewlow

[11] Patent Number: Plant 9,675

[45] Date of Patent: Oct. 29, 1996

[54] KALANCHOE PLANT NAMED MERIT

[75] Inventor: Lyndon W. Drewlow, Ashtabula, Ohio

[73] Assignee: Mikkelsens, Inc., Ashtabula, Ohio

[21] Appl. No.: 490,840

[22] Filed: Jun. 13, 1995

[51] Int. Cl.[6] ..... A01H 5/00

[52] U.S. Cl. ..... Plt./87.15

[58] Field of Search ..... Plt./87.15

*Primary Examiner*—James R. Feyrer

*Attorney, Agent, or Firm*—Foley & Lardner

[57] ABSTRACT

A new Kalanchoe cultivar named Merit characterized by the combined features of orange-red flower color, early flowering time, relatively compact plant habit, floriferous habit which produces a mounded mass of blooms, excellent keeping quality, and excellent basal branching.

1 Drawing Sheet

The present invention relates to a new and distinct cultivar of Kalanchoe plant, botanically known as *Kalanchoe blossfeldiana,* and referred to by the cultivar name Merit.

The new cultivar was developed by the inventor Lyndon W. Drewlow in a controlled breeding program carried out in Ashtabula, Ohio. The new cultivar was the result of a cross between Mikkelsen Seedling No. 88-476-4 (Seed parent) and Mikkelsen Seedling No. 88-499-1 (Pollen parent).

Subsequent asexual reproduction by stem cuttings taken by the inventor in Ashtabula, Ohio has shown that the unique features of this new Kalanchoe are stabilized and are reproduced true to type in successive propagations.

The following characteristics distinguish Merit from both its parent cultivar and other cultivated Kalanchoes of this type known and used in the floriculture industry, including the cultivars Splendor (U.S. Plant Pat. No. 7,792) and Tropicana (U.S. Plant Pat. No. 5,961), both referred to for comparison purposes.

1. Merit has a slightly lighter orange-red flower color (32A) than either Splendor (34A) or Tropicana (33A).

2. Flowering time for Merit is 3 to 5 days earlier under both summer and winter conditions than Splendor, and 5 to 7 days earlier in summer and 10 to 14 days earlier under winter conditions than Tropicana.

3. Average flower diameter of Merit is 16 mm, similar to Splendor and larger than the 14 mm diameter of Tropicana.

4. Average height of Merit is 15 to 18 cm, which is more compact than Splendor at 20 to 22 cm and Tropicana at 25 to 27 cm.

5. The leaves of Merit are 8 to 9 cm long, similar to Tropicana, but are wider, 6 to 7 cm, compared to 5.5 to 6.0 cm for Tropicana. The leaves of Splendor are larger at 10 to 11 cm in length and 9.0 to 9.5 cm in width.

6. Merit has slightly better basal branching than Splendor, and much better basal branching than Tropicana, which rarely breaks from bottom nodes.

7. Merit has a flat, crenate leaf margin. The lobe cuts of Merit are deeper than the shallow lobes of Tropicana but more shallow than the deep lobes of Splendor. Splendor also has a curled leaf.

8. The keeping quality of the flowers of Merit is 3 to 5 days longer than Splendor and 7 to 10 days longer than Tropicana. The bloom period of Merit after short day treatment is similar to Splendor and 1 week longer than Tropicana.

9. Because Merit is more compact in growth habit than Splendor, the overall appearance of Merit is a mounded mass of bloom. Splendor is more semi-upright and Tropicana very upright as a result of which the flowers are concentrated toward the top of the plants in both of the comparison cultivars.

The accompanying color photograph is a top perspective view illustrating the overall appearance of Merit, with colors being as true as it is reasonably possible to obtain in a color reproduction of this type. The photograph was taken on Mar. 31, 1995 under natural light on an overcast day under a ridged plastic greenhouse covering at Ashtabula, Ohio.

The following is a detailed description of the new cultivar, based on plants produced in greenhouses in Ashtabula, Ohio during the winter season of the year. Plants were grown in 10 cm pots and measurements were taken 16 weeks after rooted cuttings were planted. Height measurements were taken from the soil line of the container. The plants were grown at 65° to 68° F. night temperature under 3500 to 4000 foot candles of light, and with levels of 175 ppm Nitrogen, 50 ppm Potassium, and 175 PPM Phosphorous, with trace elements added. Habit of growth, plant height, flowering time, size of leaves and peduncle length are influenced by nutritional and environmental conditions.

Color references are made to The Royal Horticultural Society Colour Chart except where general terms of ordinary dictionary significance are used.

Classification:

*Commercial.*—*Kalanchoe blossfeldiana* cv. Merit.

Parentage: A controlled cross between female parent Mikkelsen Seedling No. 88-476-4 and male parent Mikkelsen Seedling No. 88-499-1.

Propagation:

*Type cutting.*—Stem tip cutting up to 3 cm long.

*Time to root.*—10 days at 21° C. summer, 14 days at 21° C. winter.

*Rooting habit.*—Abundant, fine, fibrous.

Plant description:

*Habit and form of growth.*—Compact, semi-mounded; flowers clusters above foliage; basal branching is excellent; environment and use of growth regulators will play a role in final height.

*Foliage.*—Leaves are simple and opposite. Size: Average full-grown leaves on a plant grown in a 10 cm pot are 8 to 9 cm long and 6 to 7 cm wide. Shape: Ovate, apex obtuse, base acute to rounded. Texture: Glabrous, coriaceous and succulent. Margin: Crenate, moderately lobed. Color: Young foliage, top side, 146A, under side 146B; mature foliage, top side 147A, under side 147B.

Flowering description:

*Flowering habits.*—Inflorescence is a compound dichasium (cyme). Terminal flower on main axis opens first followed by the terminal flowers of the side branches, continuing with the subsequent development of branches in the inflorescence. Inflorescence is made up of the main stem and 8 or more lateral branches.

*Natural flowering season.*—Early January. Flowering time under controlled daylength at 20° C. is 10 weeks in summer and 11½ weeks in winter. Flowering time depends on temperature, light intensity and other growing conditions.

*Flower buds.*—Oblong, up to 7 mm long before showing color; develops tubular as flower petals mature; sheathed in 4 yellow-green sepals.

*Flowers borne.*—On compound dichasial cymes. Primary peduncle 5 mm in diameter, with length varying depending on growing conditions. Pedicels vary in length depending on where they are in inflorescence.

*Quantity of flowers.*—Very floriferous since the main stem and the 8 or more lateral branches each will carry 40 or more flowers.

*Petals.*—Shape: Almost rounded, top cuspidate. Color: Top side when opening 32A, fading to 30A with 25A on the petal margins; under side 32C. Number of Petals: Four (4). Size: Individual petals are 5 mm wide and 7 mm long; flower is 16 mm in diameter.

*Reproductive organs.*—Stamens: Eight (8) in number. Anthers: Flat, elliptical, color yellow-green. Filament Color: Yellow-green. Pollen Color: Yellow. Pistils: Stigma: Flat in shape, mature color is white. Style Color: Yellow-green. Ovaries: Four (4) in number, size 6 mm, color green.

Disease resistance: Merit has shown resistance to current strains of powdery mildew which Splendor has become susceptible to. No other disease problems have been observed in Merit to date.

Other important charactertistics: Merit is an addition to a series of Kalanchoes including Majestic (U.S. Plant Pat. No. 7,794). Revelry (U.S. Plant Pat. No. 7,795), Keepsake (U.S. Plant Pat. No. 7,798), Heirloom (U.S. Plant Pat. No. 7,810), Legacy (U.S. Plant Pat. No. 9,111), Chivalry (application pending), and Empress (application pending), all of which are matched closely for flowering time, height branching and growth regulator response. This allows the domestic greenhouse grower to sell all eight colors at the same time from a single planting date and use the same growing methods on each to end up with a uniform crop. The end result is an easier crop for the grower to produce and a higher quality crop for the consumer to buy. All cultivars are ideal for 10 to 15 cm pots.

It is claimed:

1. A new and distinct cultivar of Kalanchoe plant named Merit, as illustrated and described.

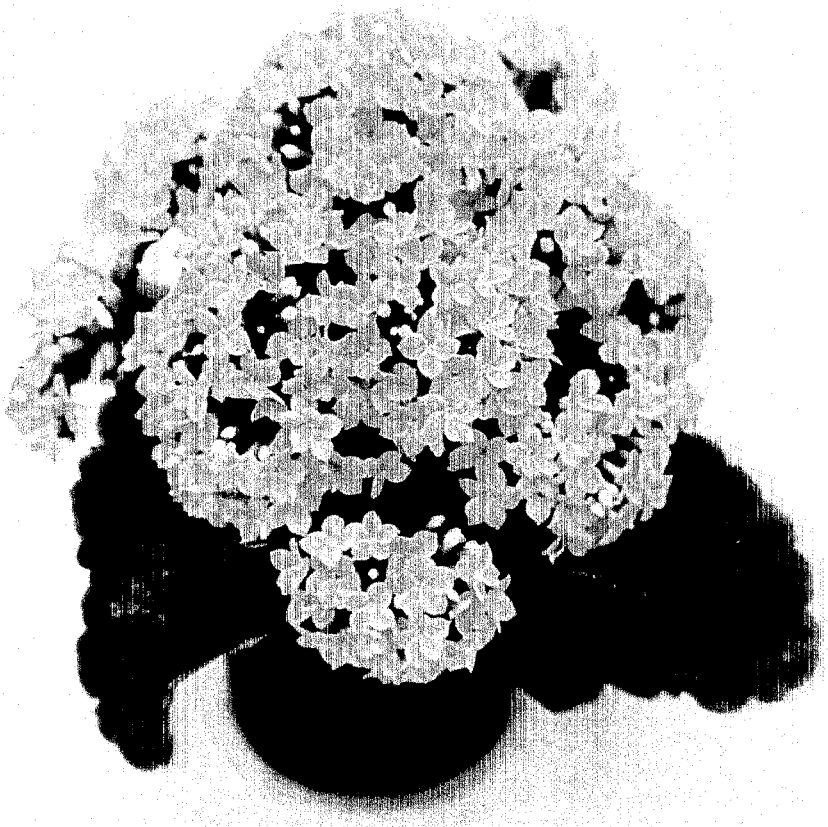

* * * * *